US006239166B1

(12) United States Patent
Black

(10) Patent No.: US 6,239,166 B1
(45) Date of Patent: May 29, 2001

(54) COMPOSITIONS FOR KILLING DUST MITES AND METHODS OF USING SAME

(76) Inventor: Robert H. Black, 4858 Mariner Point, Jacksonville, FL (US) 32225

( * ) Notice: Subject to any disclaimer, the term of this patent is extended or adjusted under 35 U.S.C. 154(b) by 0 days.

(21) Appl. No.: 09/064,526

(22) Filed: Apr. 23, 1998

Related U.S. Application Data

(60) Provisional application No. 60/044,565, filed on Apr. 24, 1997.

(51) Int. Cl.[7] .......................... A01N 43/10; A01N 37/00; A01N 37/02; A01N 37/04; C11D 3/48
(52) U.S. Cl. .......................... 514/447; 514/263; 514/264; 514/553; 514/557; 514/561; 514/566; 514/772; 514/836; 514/975; 424/DIG. 6; 510/278; 510/280; 510/319; 510/383; 8/137
(58) Field of Search ..................................... 514/263, 264, 514/447, 553, 557, 561, 566, 772, 836, 975; 424/DIG. 6; 510/278, 280, 319, 383; 8/137

(56) References Cited

U.S. PATENT DOCUMENTS

| 3,401,007 | * | 9/1968 | Hoffmann et al. ........................ 8/137 |
| 3,919,101 | * | 11/1975 | Anstett et al. ........................ 510/279 |
| 5,030,658 | | 7/1991 | Salloum et al. ........................ 514/560 |
| 5,536,452 | | 7/1996 | Black ........................ 252/238 |
| 5,587,022 | | 12/1996 | Black ........................ 134/26 |
| 5,985,273 | * | 11/1999 | Reed et al. ........................ 424/94.63 |

FOREIGN PATENT DOCUMENTS

| 86/01724 | * | 3/1986 | (WO) . |
| 89/12673 | * | 12/1989 | (WO) . |
| 97/32949 | * | 9/1997 | (WO) . |

OTHER PUBLICATIONS

CROPU Abstract, accession No. 86–80743, 1984.*
Chemical Abstracts 102:77934q, 1985.*
Chemical Abstracts 104:7514v, 1986.*
Chemical Abstracts 105:56367, Aug. 1986.*

* cited by examiner

Primary Examiner—John Pak
(74) Attorney, Agent, or Firm—Browdy And Neimark

(57) ABSTRACT

The invention relates to an aqueous pesticide composition for killing dust mites, which contains a chelating agent as the active ingredient and a surfactant to facilitate distribution over, or subsequent removal from, the surfaces of fabric or fibrous materials, such as floor coverings, wall and window coverings, furniture coverings, etc. The invention also relates to methods of using the aqueous pesticide composition for killing dust mites and controlling the dust mite population in the indoor living environment and for cleaning carpets and rugs.

17 Claims, No Drawings

US 6,239,166 B1

COMPOSITIONS FOR KILLING DUST MITES AND METHODS OF USING SAME

CROSS-REFERENCE TO RELATED APPLICATIONS

The present application claims priority under 35 USC §119(e) from U.S. provisional application No. 60/044,565, filed Apr. 24, 1997, the entire contents of which are hereby incorporated by reference.

BACKGROUND OF THE INVENTION

1. Field of the Invention

The present invention relates to a composition for killing and/or controlling dust mites and methods of using same.

2. Description of the Related Art

Dust mites, which inhabit the fabric or fibrous material used in floor coverings, wall and window coverings, furniture, bedding and clothing, are the constant companions of humans in the indoor living and working environment. They live off the sheddings of human skin and other debris which are abundantly available as a result of normal human activity. However, despite this abundance of food, the dust mites live in a "desert" environment in which the only source of water to sustain life comes from the moisture in the air.

It is the feces of these dust mites that have been identified as the major cause of allergic reactions and asthma in susceptible individuals who have been previously sensitized to such dust mite allergens. For these sensitive individuals, part of the solution to preventing allergic reactions and asthma attacks is avoidance of dust mite allergens by controlling the population of dust mites in the indoor living and working environment. Typically, the measures used to control dust mites include (1) eliminating floor coverings, furniture, drapes and wall coverings made from fabric or fibrous materials, (2) washing the bedding and clothing with disinfectant, and (3) frequent cleaning of all hard surfaces. Conventional insecticides are not generally used for this type of application due to safety/toxicity concerns.

SUMMARY OF THE INVENTION

It is accordingly an object of the present invention to provide an aqueous pesticide composition, which kills dust mites, thereby controlling the dust mite population in the indoor living and working environment, without exposing individuals to toxic substances.

The aqueous pesticide composition according to the present invention contains a chelating agent as the active ingredient and a surfactant to facilitate the uniform distribution of the active ingredient over fiber surfaces of fabrics and fibrous materials and/or the cleansing of the fibers.

Another object of the present invention is to provide a method for controlling or killing dust mites in an indoor living or working environment by applying the aqueous pesticide composition of the present invention to surfaces of fabric and fibrous materials.

A further object of the present invention is a method for killing dust mites which also serves to clean carpets and rugs.

DETAILED DESCRIPTION OF THE INVENTION

The aqueous pesticide composition in accordance with the present invention contains a metal ion chelating agent as the active ingredient and a surfactant for distributing the active ingredient over the fiber surfaces of fabric or fibrous materials and/or to effect a cleansing action on the fibers.

As the active ingredient in the aqueous pesticide composition of the present invention, the chelating agent acts to interrupt the metabolic activity of dust mites that have come into contact with the chelating agent by chelating metal ions and minerals to make them unavailable for dust mite metabolism. Dust mites are unable to overcome this toxic effect of the chelating agent because the lack of water in the dust mites' "desert" environment prevents them from eliminating the chelating agent from their system by excretion. Thus, while water obtained from the moisture in the air is sufficient for dust mites to survive their dry environment, it is, however, inadequate for allowing dust mites to avoid the toxic effect of the chelating agent contained in the aqueous pesticide composition of the present invention.

Any of a large number of metal ion/mineral chelating agents well-known in the art may be used as the active ingredient so long as the chelating agent is soluble in an aqueous solution in the range of about 0.5 to 8% by weight, more preferably in the range of about 1 to 4%, and the chelating agent is not toxic to humans and pets in the amounts present on the applied surfaces. It is expected that most, if not all, metal ion/mineral chelating agents would be effective in interrupting dust mite metabolism. Preferred chelating agents include ethylene diamine tetraacetic acid (EDTA), diethylene triamine pentacetic acid (DTPA), nitrilotriacetic acid (NTA), hydroxyethyl ethylene diamine triacetic acid (HEEDTA), and salts thereof. The most preferred chelating agents are EDTA and salts thereof.

The choice of the surfactant present in the aqueous pesticide composition depends on whether the aqueous pesticide composition is to be applied to fabrics or fibrous materials, such as drapes, furniture coverings, bedding and clothing, carpets, rugs, etc., and left thereon as residues, or whether it is to be applied to carpets and rugs as a combination pesticide/cleaner. When a fabric or fibrous material is to be treated so that the active chelating agent is left as a residue on the surfaces of the fibers, the surfactant is any of a number of surfactants capable of evenly spreading the active chelating agent component of the composition over the surfaces of the fibers in the fabric covering. A super wetting surfactant (agent), such as but not limited to, a polyethylene oxide monoallyl ether in the class of silicone glycol copolymers (e.g., Q2-5211 and Q2-5212 from Dow Corning), is preferred. Another example of a suitable surfactant is a fluorinated anionic surfactant marketed by E.I. du Pont de Nemours & Company under the name ZONYL FSP. All suitable super wetting surfactants have the property of being effective, in small quantities such as in the range of about 0.001 to 0.2% by weight, more preferably in the range of about 0.05 to 1.5%, in uniformly distributing the chelating agent over the surfaces of the fibers in the fabric or fibrous material to provide a residual film of chelating agent without forming any sticky deposits.

In the case of an aqueous pesticide composition which can be used for cleaning carpets and rugs, the surfactant is any of a number of suitable surfactants that can be applied as a component in the range of about 1 to 10% by weight, more preferably in the range of about 2 to 5% of the aqueous pesticide composition, using standard conventional carpet cleaning equipment, and that have the property of forming of friable deposits which can be readily collected with a household vacuum cleaner. A non-limiting preferred example of such a suitable surfactant is lauric monoethanolamide sodium sulfosuccinate, manufactured and marketing by Rhone-Poulenc, Cranbury, N.J. under the designation SS-L9ME, and available as a 40% active white paste.

For both the aqueous pesticide and pesticide cleaner compositions, an alkaloid stimulant, such as caffeine, theophylline, and theobromine, which serves to further stress dust mites can be optionally added. When present in the aqueous composition, such an alkaloid stimulant is added in the range of about 0.05 to 1% by weight. While these alkaloid stimulants are toxic to dust mites, they have relatively low toxicity to humans and pets, particularly at the levels applied to fabric and fibrous materials.

The pH of the aqueous pesticide composition, which is adjusted as needed, is preferably between about 4 and 7, and any subranges thereof, and which suitably allows the chelating agent to be soluble in the aqueous pesticide composition.

A preferred embodiment of the aqueous pesticide composition, expressed in percent (%) by weight, for treating fabric and fibrous material coverings is as follows:

| | |
|---|---|
| disodium ethylene diamine tetracetic acid | 2% |
| Q2-5212 super wetting surfactant (polyethylene oxide monoallyl ether) | 0.01% |
| water | balance |

A preferred embodiment of the aqueous pesticide composition used for cleaning carpets and rugs, expressed in percent (%) by weight, is as follows:

| | |
|---|---|
| tetrasodium ethylenediamine tetraacetic acid | 2% |
| SS-L9ME anionic surfactant (in terms of 100% lauric monoethanolamide sodium sulfosuccinate) | 3% |
| water | balance |

In accordance with the present invention, the method of killing dust mites and controlling the dust mite population in an indoor living and working environment involves applying by any suitable means, i.e., spraying, etc., to fabric or fibrous material coverings the aqueous pesticide composition of the present invention. The aqueous pesticide composition may be reapplied as needed, particularly if the fiber surfaces are exposed to direct sunlight, whose ultraviolet rays can degrade the active chelating agent over time.

The method of cleaning carpets with the aqueous pesticide composition according to the present invention involves applying the aqueous pesticide/carpet cleaning composition to carpets or rugs by spraying, by using standard carpet cleaning equipment, or by any other suitable means. The friable residue formed by the surfactant in the aqueous pesticide/carpet cleaning composition is later removed by vacuuming. For carpets and rugs, the method of killing dust mites and controlling the dust mite population in the indoor living and working environment may be combined with the method of cleaning carpets with an aqueous pesticide/carpet cleaning composition.

Generally, however, when carpets or rugs are cleaned by the method according to the present invention, or for that matter by any other carpet cleaning method, it is recommended that the aqueous pesticide composition, containing the superwetting surfactant for uniformly distributing the active chelating agent over fiber surfaces, be reapplied by the method of killing dust mites and controlling dust mite populations according to the present invention. This reapplication is to ensure that the fiber surfaces of the carpet or rug continue to have an even distribution of the active chelating agent which may have been removed in the carpet cleaning process. Thus, the combination of the method of killing dust mites and the method of cleaning carpets or rugs according to the present invention not only kills dust mites, but also maintains a clean carpet or rug.

The foregoing description of the specific embodiments will so fully reveal the general nature of the invention that others can, by applying current knowledge, readily modify and/or adapt for various applications, such specific embodiments, without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. An aqueous pesticide composition for dust mites consisting essentially of:

about 0.5 to 8% by weight of a chelating agent selected from the group consisting of ethylene diamine tetraacetic acid (EDTA), diethylene triamine pentaacetic acid (DPTA), nitrilotriacetic acid (NTA), hydroxyethyl ethylene diamine triacetic acid (HEEDTA), and salts thereof;

about 0.001 to 10% by weight of a surfactant, wherein the surfactant is (i) a super wetting agent selected from the group consisting of a silicone glycol copolymer and a polyethylene oxide monoallyl ether, or (ii) a surfactant having the property of forming a friable residue;

water; and optionally an alkaloid stimulant.

2. The aqueous pesticide composition according to claim 1, wherein the surfactant is said super wetting surfactant and said super wetting surfactant is present in the range of about 0.001 to 0.2% by weight.

3. The aqueous pesticide composition according to claim 2, wherein said super wetting surfactant is a silicone glycol copolymer.

4. The aqueous pesticide composition according to claim 2, wherein said super wetting surfactant is a polyethylene oxide monoallyl ether.

5. The aqueous pesticide composition according to claim 4, consisting essentially of:

about 2% by weight salt of ethylene diamine tetraacetic acid as a chelating agent;

about 0.01% by weight polyethylene oxide monoallyl ether; and water.

6. The aqueous pesticide composition according to claim 1, wherein the surfactant is said surfactant having the property of forming a friable residue and said surfactant is present in the range of about 1 to 10% by weight.

7. The aqueous pesticide composition according to claim 6 wherein said range is about 2 to about 5% by weight.

8. The aqueous pesticide composition according to claim 6, wherein said surfactant having the property of forming a friable residue is lauric monoethanolamide sodium sulfosuccinate.

9. The aqueous pesticide composition according to claim 8, consisting essentially of:
about 2% by weight salt of ethylene diamine tetraacetic acid as a chelating agent;
about 3% by weight lauric monoethanolamide sodium sulfosuccinate; and
water.

10. The aqueous pesticide composition according to claim 1, consisting essentially of:
about 2% by weight salt of ethylene diamine tetraacetic acid as a chelating agent;
about 3% by weight lauric monoethanolamide sodium sulfosuccinate;
water; and
about 0.05–1% by weight of an alkaloid stimulant.

11. The aqueous pesticide composition according to claim 1, wherein an alkaloid stimulant is present in a range of about 0.05 to 1.0% by weight.

12. The aqueous pesticide composition according to claim 11, wherein said alkaloid stimulant is selected from the group consisting of caffeine, theophylline, and theobromine.

13. The aqueous pesticide composition according to claim 1 wherein said surfactant is either a super wetting surfactant present in the range of about 0.001 to about 1.5% by weight, or a surfactant having the property of forming a friable residue, present in the range of about 1 to about 10% of weight.

14. The aqueous pesticide composition according to claim 1 wherein said chelating agent is present in the range of about 1 to about 4% by weight.

15. A method of killing dust mites on fabric or fibrous material coverings, comprising the step of:
applying an aqueous pesticide composition according to claim 2 to a fabric or fibrous material covering to form a dry pesticide deposit whereby dust mites are killed after contact with the dry pesticide deposit.

16. The method according to claim 15, wherein the fabric or fibrous material covering is a carpet or rug.

17. A method of killing dust mites on a carpet or rug, comprising the steps of:
applying an aqueous pesticide composition according to claim 6 to a carpet or rug; and
vacuuming.

* * * * *